(12) United States Patent
Alanbaei

(10) Patent No.: US 11,395,644 B2
(45) Date of Patent: Jul. 26, 2022

(54) SINUS VENOSUS ATRIAL SEPTAL DEFECT TREATMENT DEVICE

(71) Applicant: Muath Alanbaei, Safat (KW)

(72) Inventor: Muath Alanbaei, Safat (KW)

(73) Assignee: Gulf Medical Technologies, Kuwait (KW)

(*) Notice: Subject to any disclaimer, the term of this patent is extended or adjusted under 35 U.S.C. 154(b) by 727 days.

(21) Appl. No.: 16/191,612

(22) Filed: Nov. 15, 2018

(65) Prior Publication Data
US 2019/0083076 A1 Mar. 21, 2019

Related U.S. Application Data

(63) Continuation-in-part of application No. 15/891,653, filed on Feb. 8, 2018, now Pat. No. 10,531,867.
(Continued)

(51) Int. Cl.
*A61B 17/00* (2006.01)
*A61F 2/07* (2013.01)
(Continued)

(52) U.S. Cl.
CPC .......... *A61B 17/0057* (2013.01); *A61F 2/07* (2013.01); *A61F 2/958* (2013.01);
(Continued)

(58) Field of Classification Search
CPC .......... A61B 2017/00243; A61B 2017/00606; A61B 2017/0055; A61B 2017/00575; A61B 2017/00592; A61B 2017/00597; A61B 2017/00619; A61B 2017/00623; A61B 17/0057; A61F 2/821; A61F 2/825; A61F 2/90; A61F 2/958; A61F 2/06;
(Continued)

(56) References Cited

U.S. PATENT DOCUMENTS

| 8,147,513 B2 | 4/2012 | Siebold et al. |
| 9,604,036 B2 | 3/2017 | Burton et al. |
(Continued)

FOREIGN PATENT DOCUMENTS

| AU | 2013/270508 A | 1/2014 |
| EP | 2108315 A2 | 10/2009 |
(Continued)

*Primary Examiner* — Sarah W Aleman
(74) *Attorney, Agent, or Firm* — Winthrop & Weinstine, P.A.; Nadeem W. Schwen

(57) ABSTRACT

Devices and methods for treating a sinus venosus atrial septal defect. A treatment device may have a tubular shape and may be configured to be arranged to provide a conduit between an upper right pulmonary vein (PV) and a left atrium (LA). The device may have a proximal portion comprising a flexible mesh configured to anchor within the LA, a distal portion comprising a flexible mesh configured to anchor within the target PV, and a central portion having a plurality of elongate parallel bars. A method for treating a sinus venosus atrial septal defect may include percutaneously advancing the device through the femoral vein and inferior vena cava (IVC), and into the right atrium (RA). The method may include creating a trans-septal opening, passing the device through the opening into the LA, and toward the upper right PV to treat the defect.

9 Claims, 11 Drawing Sheets

Related U.S. Application Data

(60) Provisional application No. 62/458,527, filed on Feb. 13, 2017.

(51) Int. Cl.
*A61F 2/958* (2013.01)
*A61F 2/06* (2013.01)
*A61F 2/82* (2013.01)
*A61B 90/00* (2016.01)
*A61B 17/11* (2006.01)

(52) U.S. Cl.
CPC ............... *A61B 2017/00557* (2013.01); *A61B 2017/00575* (2013.01); *A61B 2017/00592* (2013.01); *A61B 2017/00597* (2013.01); *A61B 2017/00615* (2013.01); *A61B 2017/00619* (2013.01); *A61B 2017/00623* (2013.01); *A61B 2017/00853* (2013.01); *A61B 2017/1107* (2013.01); *A61B 2090/3966* (2016.02); *A61F 2002/061* (2013.01); *A61F 2002/825* (2013.01); *A61F 2002/9583* (2013.01)

(58) Field of Classification Search
CPC ............. A61F 2/07; A61F 2002/9505; A61F 2002/9582; A61F 2002/9583; A61F 2002/821

See application file for complete search history.

(56) References Cited

U.S. PATENT DOCUMENTS

| | | | |
|---|---|---|---|
| 2007/0055358 A1* | 3/2007 | Krolik | A61F 2/915 623/1.31 |
| 2007/0244494 A1 | 10/2007 | Downing | |
| 2007/0270741 A1 | 11/2007 | Hassett et al. | |
| 2008/0077224 A1* | 3/2008 | Valencia | A61M 25/1027 623/1.11 |
| 2009/0306685 A1* | 12/2009 | Fill | A61B 17/12131 606/148 |
| 2011/0022151 A1 | 1/2011 | Shin et al. | |
| 2011/0130619 A1* | 6/2011 | Whisenant | A61M 60/135 600/16 |
| 2013/0261734 A1 | 10/2013 | Young et al. | |
| 2013/0317541 A1 | 11/2013 | Singhal et al. | |
| 2014/0277119 A1 | 9/2014 | Akipinar | |
| 2014/0288480 A1* | 9/2014 | Zimmerman | A61F 2/848 606/108 |
| 2014/0343602 A1 | 11/2014 | Cox et al. | |
| 2015/0039004 A1 | 2/2015 | Sarge | |
| 2015/0119931 A1 | 4/2015 | Amplatz et al. | |

FOREIGN PATENT DOCUMENTS

| | | |
|---|---|---|
| GB | 2378137 A | 2/2003 |
| KR | 10-2009-0122721 A | 12/2009 |
| SU | 407555 | 12/1973 |

* cited by examiner

SINUS VENOSUS ATRIAL SEPTAL DEFECT TREATMENT DEVICE

CROSS-REFERENCE TO RELATED APPLICATION

This application claims priority to U.S. Non-Provisional patent application Ser. No. 15/891,653, titled Sinus Venosus Atrial Septal Defect Treatment Device and filed Feb. 8, 2018, and U.S. Provisional Patent Application Ser. No. 62/458,527, titled Sinus Venosus Atrial Septal Defect Treatment Device and filed Feb. 13, 2017, the content of each of which is hereby incorporated by reference herein in its entirety.

FIELD

The present disclosure relates to a percutaneous interventional device, and particularly to a sinus venosus atrial septal defect treatment device and method.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Typically, in a normal functioning heart, the left atrium receives oxygenated blood from each of the four pulmonary veins. After receiving it, the oxygenated blood flows into the left ventricle, where the oxygenated blood is subsequently pumped to the brain, organs, and tissues of the body. The right atrium, on the other hand, receives deoxygenated blood from the superior vena cava and inferior vena cava and other cardiac veins and then pumps deoxygenated blood into the right ventricle, which subsequently pumps the deoxygenated blood into the pulmonary system to replenish its oxygen supply. Normally, the left atrium and the right atrium are separated by a septum known as the interatrial septum that prevents the oxygenated blood in the left atrium from mixing with the deoxygenated blood in the right atrium.

However, if the interatrial septum fails to properly develop, an atrial septal defect (ASD) can result. An ASD is a hole in the interatrial septum that allows the oxygenated blood to mix with the deoxygenated blood. If the ASD is left untreated, it can lead to lower than normal oxygen in the atrial blood that is pumped from the left atrium to the brain, organs, and tissues of the body, which can eventually lead to the development of a cardiac arrhythmia, decompression sickness, Eisemnenger's syndrome, paradoxical embolus, and even migraines.

There are four types of ASDs, an ostium secundum ASD, an ostium primum ASD, a sinus venosus ASD, and a coronary sinus ASD, the ostium secundum ASD being the most prevalent. While ostium secundum and ostium primum ASDs account for approximately 70% and 20%, respectively, of the total number of ASDs, sinus venosus ASDs account for approximately 10% of the total number of ASDs. The most common type of sinus venosus ASD occurs at the junction of right atrium and the superior vena cava, which is the location where the pulmonary veins enter the heart. In other words, one of the four pulmonary veins, such as the right upper pulmonary vein, drains into the right atrium instead of the left atrium. While ostium secundum ASD can be treated percutaneously, as well as surgically, to date, there is no percutaneous interventional procedure for treating sinus venosus ASDs percutaneously. Additionally, surgical repairs can lead to longer recovery times, higher risk of infection, and other undesirable outcomes.

SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure, in one or more embodiments, relates to a device for treating a sinus venosus atrial septal defect. The device may include a hollow lumen extending between first and second open ends. The lumen may be defined by a cylindrical sidewall and may have a proximal portion, a distal portion, and a central portion. The proximal portion may be arranged at the first open end and may include a self-expanding mesh. The proximal portion may further be sized and configured to be arranged within the left atrium, and may be configured to anchor to a wall of the left atrium. The distal portion may be arranged at the second end and may include a self-expanding mesh. The distal portion may be sized and configured to be arranged within a pulmonary vein, and may be configured to anchor to a wall of the pulmonary vein. The central portion may extend between the proximal and distal portions, and may include a plurality of elongate parallel bars surrounded by a coating. The central portion may be sized and configured to be arranged within a right atrium, and may be configured to provide a conduit for blood flow between the pulmonary vein and the left atrium. In some embodiments, the proximal portion may be configured to expand to a bell-shaped skirt, and the proximal portion may have an expandable septal augmenter rim arranged at the first open end. The device may have a coating arranged over at least a portion of the proximal portion and at least a portion of the distal portion. The sidewall of the device may have a wave-shaped cross sectional shape. In some embodiments, the device may have at least one locking mechanism for engaging with a locking system during insertion of the device into a pulmonary vein. The locking mechanism may include at least one keyhole configured to receive a corresponding key. Additionally, in some embodiments, the device may have an aperture in the sidewall. The aperture may be surrounded by a radio-opaque material.

The present disclosure, in one or more embodiments, additionally relates to a system for treating a sinus venosus atrial septal defect. The system may include a sinus venosus atrial septal defect treatment device, a balloon catheter, and a locking system. The treatment device may have a hollow lumen extending between first and second open ends. The lumen may be defined by a cylindrical sidewall and may be sized and configured for being arranged between a pulmonary vein and a left atrium. The treatment device may additionally have a keyhole arranged on the sidewall and configured to receive a corresponding key. The balloon catheter may have an inflatable balloon portion, and may be sized and configured for being passed through a left atrium and into a pulmonary vein. The locking system may be arranged on the balloon catheter and may be configured for securing the treatment device to the balloon catheter. The locking system may include a key for engaging with the keyhole. In some embodiments, the keyhole may include a first portion and a second portion. Additionally, the treatment device may include a proximal portion sized and configured to be arranged within the left atrium, and a distal portion sized and configured to be arranged within the pulmonary vein. In some embodiments, the keyhole may be arranged on the distal portion of the treatment device.

The present disclosure, in one or more embodiments, additionally relates to a method of treating a sinus venosus atrial septal defect in a patient. The method may include the steps of advancing a sheath through a femoral vein and inferior vena cava of the patient, toward an interatrial septum of the patient. Additionally, the method may include, from a right atrium of the patient, making a trans-septal opening in the interatrial septum, and, from a left atrium of the patient, positioning a hollow lumen between the left atrium and a pulmonary vein of the patient to bridge the sinus venosus atrial septal defect. Positioning a hollow lumen between the left atrium and a pulmonary vein of the patient may include arranging a distal portion of the lumen in the pulmonary vein and arranging a proximal portion of the lumen in the left atrium, wherein a central portion of the lumen is arranged within the right atrium to provide a conduit for blood flow between the pulmonary vein and the left atrium. In some embodiments, the method may include using imaging to visualize the hollow lumen within the patient. The treatment device may have a sidewall aperture, and where the pulmonary vein is branched, the method may include extending a bridge between the branch of the pulmonary vein and the aperture so as to provide a conduit for blood flow from the branch of the pulmonary vein to the treatment device. In some embodiments, the method may be performed while the patient is under general anesthesia. The method may include sealing the trans-septal opening. Moreover, the hollow lumen may be removable, and the method may include accessing the hollow lumen through the left atrium or right atrium to remove the hollow lumen by capturing the hollow lumen through the locking mechanism. The method may include positioning the lumen over a balloon catheter and inflating the balloon catheter to expand a diameter of the lumen. Additionally, the method may include locking the lumen to the balloon catheter and, after the lumen is positioned between the left atrium and pulmonary vein of the patient and expanded, disengaging the lumen from the balloon catheter.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The present disclosure relates to devices and methods for treating a sinus venosus atrial septal defect. In particular, the present disclosure relates to a device having a tubular shape and configured to be arranged to provide a conduit between an upper right pulmonary vein (PV) and a left atrium (LA). The device may have a proximal portion comprising a flexible mesh and configured to be arranged and anchored within the LA, a distal portion comprising a flexible mesh and configured to be arranged and anchored within the target PV, and a central portion extending between the proximal and distal portions. The central portion may have a plurality of elongate parallel bars configured to provide a bridge across the right atrium (RA). Moreover, the device, or portions thereof, may be expandable and collapsible. Additionally, the present disclosure relates to a method for treating a sinus venosus atrial septal defect using a device of the present disclosure. In particular, the method includes steps for implanting or arranging the device between a target PV and the LA. The method may be a percutaneous method wherein the device is passed via a sheath through the femoral vein and inferior vena cava (IVC), and into the right atrium (RA). The method may include creating a trans-septal opening, passing the device through the opening into the LA, and toward the upper right PV to treat the defect.

Figure 1A:
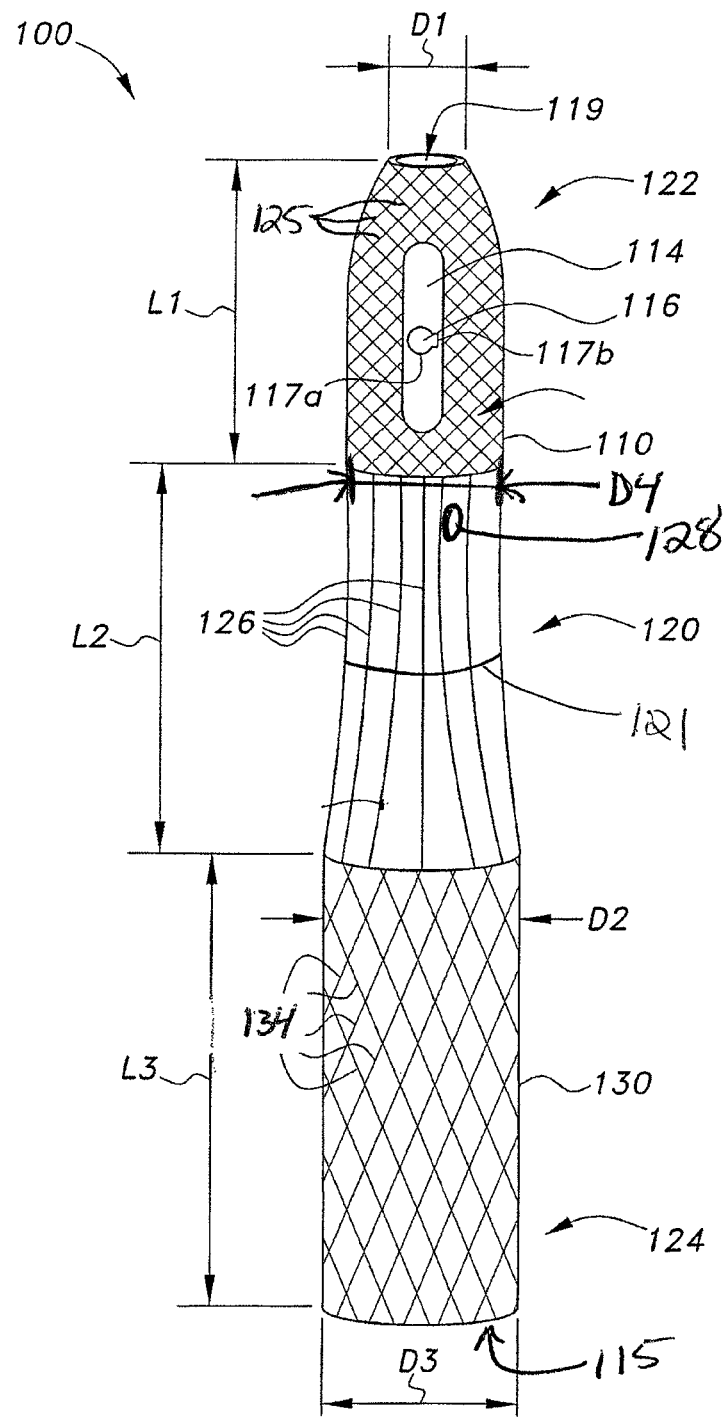
FIG. 1A is an environmental side view of an atrial septal defect treatment device in collapsed form, according to one or more embodiments.
Figure 1B:
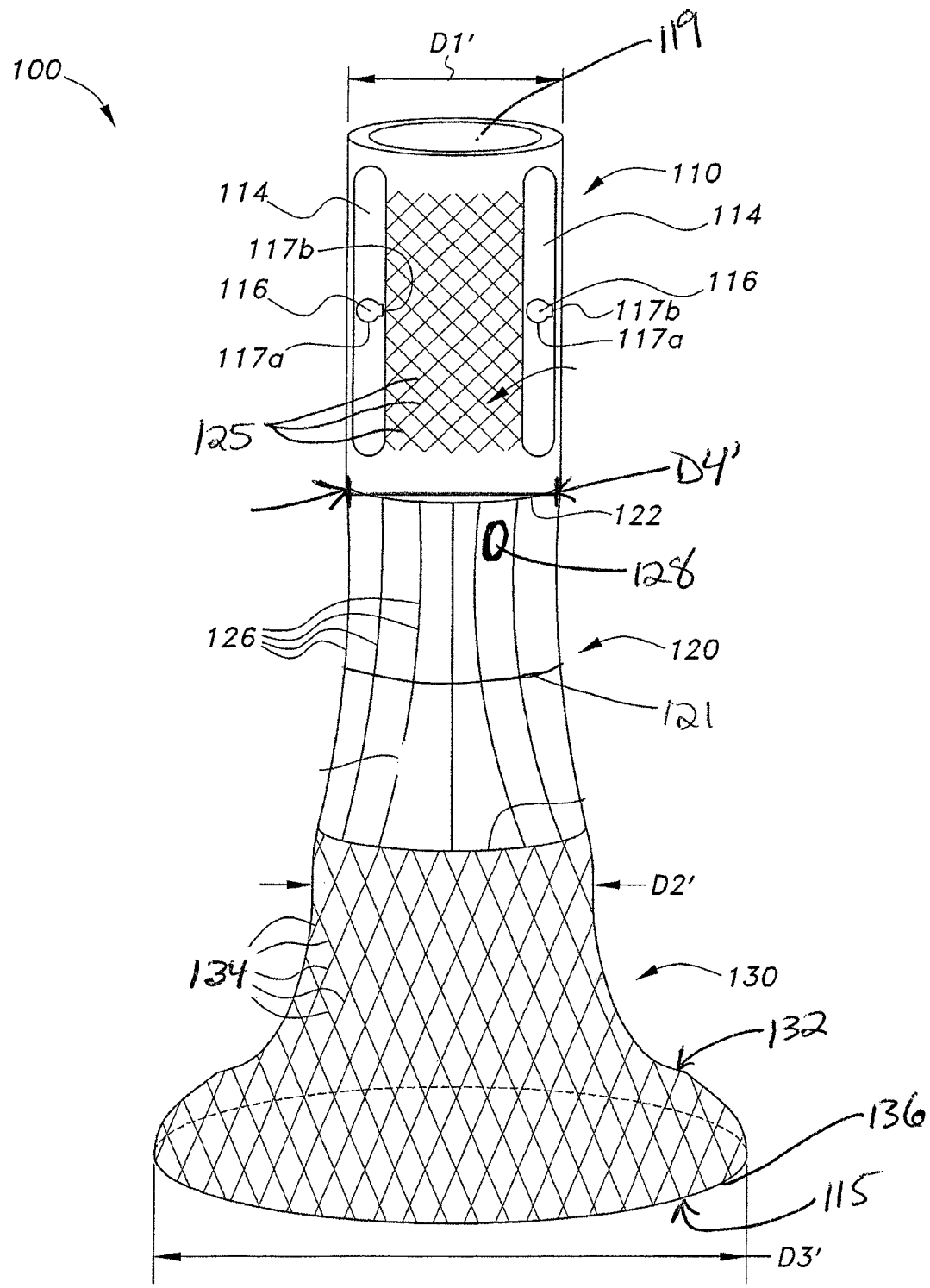
FIG. 1B is another environmental side view of the atrial septal defect treatment device of FIG. 1A in expanded form, according to one or more embodiments.
Figure 1C:
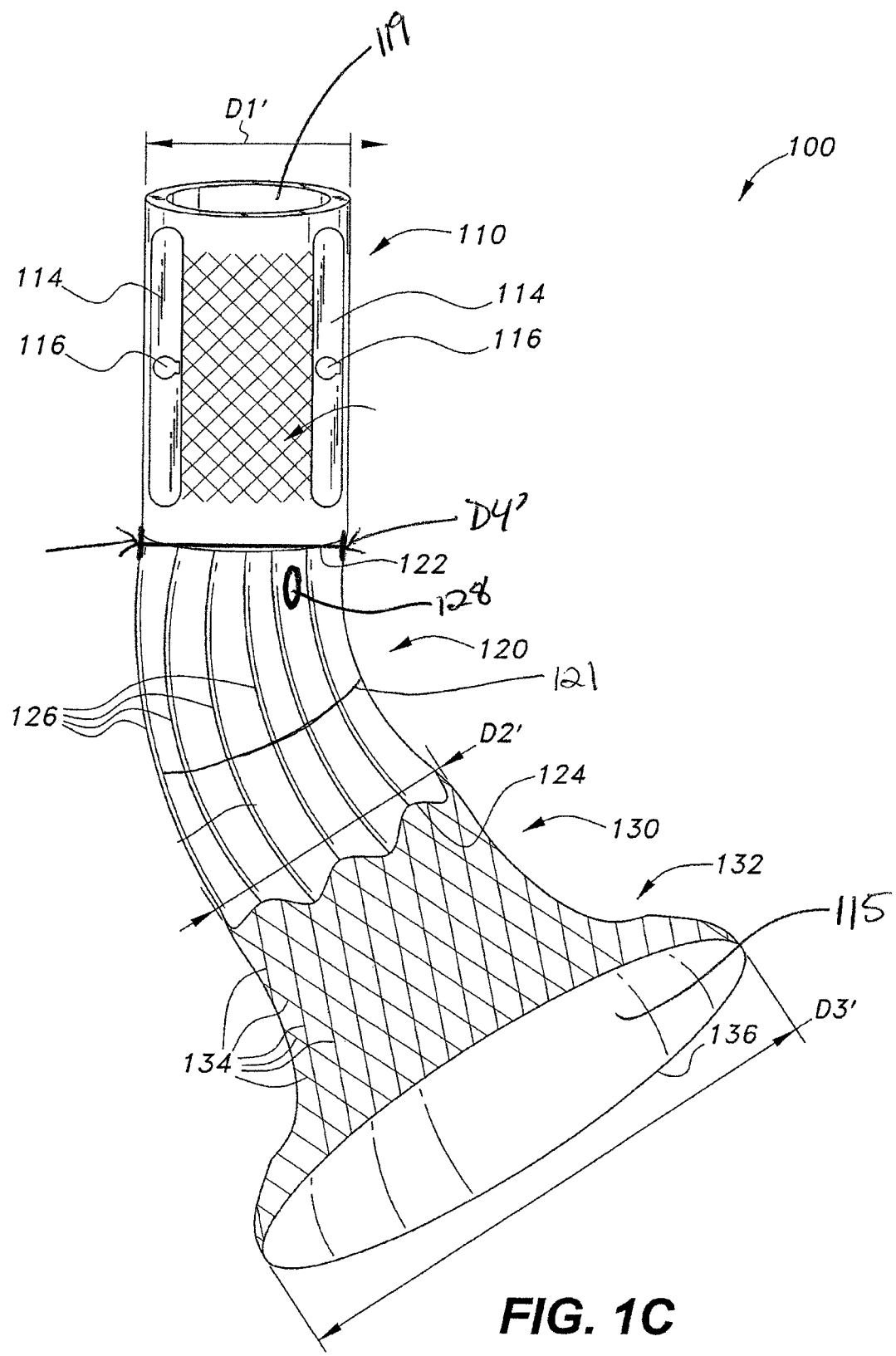
FIG. 1C illustrates a configuration of the atrial septal defect device of FIG. 1A expanded within a pulmonary vein of a heart, according to one or more embodiments.

Turning now to FIGS. 1A-1C, an atrial septal defect treatment device 100, configured for the percutaneous closure of a sinus venosus atrial septal defect for diversion of anomalous pulmonary drainage into the left atrium, is generally illustrated. The device 100 may be or include a hollow lumen with openings 115, 119 at each of two ends 124, 122. In some embodiments, the device 100 may have a generally tubular or funnel shaped configuration extending between a first end 124 and a second end 122. The device 100 may be configured to be inserted at least partially in the right upper PV, and may further be configured to extend from the PV to the LA to provide a bridge across or through the RA. The first end 124 of the device 100 may be configured to expand in a skirt-like or bell-shaped configuration once the device 100 is positioned such that the second end 122 is in the right upper PV. In this manner, the device 100 may be configured to close an upper sinus venosus hole and divert anomalous pulmonary venous drainage into the left atrium. As shown in FIGS. 1A-1C, the device 100 may have a proximal portion 130, a distal portion 110, and a central portion 120 arranged between the proximal and distal portions.

As shown in FIG. 1A, the proximal portion 130 may be arranged and configured such that, as a medical professional inserts the second end 122 into the right upper PV, the proximal portion may be closest to the medical professional. The proximal portion 130 may have a generally tubular shape extending between the opening 115 at the first end 124 and the central portion 120. The proximal portion 130 may be configured to be arranged within the LA, or at least partially within the LA, so as to allow blood flow from the right upper PV to drain into the LA. The proximal portion 130 may have a length L3 of between approximately 1 mm and approximately 30 mm, or between approximately 5 mm and approximately 15 mm, or between approximately 8 mm and approximately 12 mm. In at least one embodiment, the proximal portion 130 may have a length of 10 mm or approximately 10 mm. The proximal portion 130 may have a diameter D2 arranged at a point along its length. In some embodiments, the diameter D2 may be between approximately 0.5 mm and approximately 30 mm or approximately 5 mm to approximately 20 mm. At the first end 124, the proximal portion 130 may define an opening 115 having a diameter D3. In some embodiments, the diameter D3 may be between approximately 0.5 mm and approximately 40 mm or approximately 15 mm to approximately 30 mm. Still other length and diameter combinations may be provided to create a tubular or funnel shape and accommodate the anatomy.

The proximal portion 130 may be constructed of one or more flexible materials. Additionally, proximal portion 130 may be configured to expand and/or contract. For example, the proximal portion 130, or a portion thereof, may be constructed of an expandable mesh material comprising a plurality of interlocking web members 134 or wires arranged in a grid formation. The web members 134 may be metal bars or wires, such as Nitinol members, in some embodiments. In other embodiments, the web members 134 may be constructed of other suitable materials. Additionally, the proximal portion 130, or a portion thereof, may have a coating or covering arranged over or across the mesh so as to prevent leakage between the web members 134. However, in other embodiments, the web members 134 may be arranged over or across the coating material. The coating may be or include polytetrafluoroethylene and/or another suitable medical grade material. In some embodiments, a portion of the proximal portion 130 nearest the central portion 120 may be coated. For example, approximately ⅕, ¼, or ⅓ the length of the proximal portion 130 nearest the central portion 120 may be coated. In some embodiments, approximately half the length of the proximal portion 130 may be coated. In still other embodiments, more than half or all of the proximal portion 130 may be coated. In some embodiments, the coating may be applied when the device is in an expanded position. When the device is collapsed, the coating may collapsed and/or it may bunch up and/or wrinkle such that the self-expanding device is not inhibited from expanding at the desired time.

The mesh material, or other expandable material(s), may allow the proximal portion 130, or a portion thereof, to expand and contract radially, thus increasing and/or decreasing diameters D2 and D3. For example, the interlocking web members 134 may be configured to expand apart, thus increasing gaps or openings between the bars and causing the proximal portion 130 to expand radially. In some embodiments, the proximal portion 130 may be configured to expand more at the first end 124 than at the connection to the central portion 120. FIGS. 1B and 1C show the proximal portion 130 in an expanded configuration with expanded diameters D2' and D3'. The expanded diameter D3' of the opening 115 may be between approximately 10 mm and approximately 40 mm, or between approximately 20 mm and approximately 35 mm. The expanded diameter D2' may be arranged at or near a connection between the proximal portion 130 and the central portion 120. The expanded diameter D2' may be larger than D2, but smaller than D3'. The expanded diameter D2' may be between approximately 5 mm and approximately 30 mm or approximately 10 mm and approximately 20 mm. Between the portion of the proximal portion 130 having expanded diameter D2' and the opening 115 having expanded diameter D3', the proximal portion may have a curved wall forming a bell-shaped or cone-shaped skirt 132.

In some embodiments, the proximal portion 130 may be configured to expand automatically. For example, the skirt 132 may have a tendency to expand when not being actively compressed. In at least one embodiment, the web members 134, or portions thereof, may be heat-treated so as to cause the mesh to expand automatically. For example, heat treating Nitinol may allow it to have a memory shape. In some embodiments, when compressed, the skirt 132, or portions thereof, may have a wave-shaped or zig-zagged perimeter wall. The wave-shape may be a function of compression of the interlocking web members 134. In some embodiments, the proximal portion 130 may be configured to expand when positioned in the LA to occlude the sinus venosus atrial septal defect (e.g. opening) from the LA side of the interatrial septum (IS).

The proximal portion 130 may be configured to be arranged within the LA, or within a portion thereof, so as to allow blood flow to drain into the LA. In some embodiments, the proximal portion 130 may be configured to engage with, or anchor to, an inner wall or edge of the LA so as to maintain a desired position of the device 100. In this way, the mesh material may be configured to attach or anchor into an inner wall of the LA. Additionally, at the expandable opening 115, the proximal portion 130 may have a septal augmenter rim 136 configured for securing the device 100 in place within the heart. In particular, the rim 136 may be configured to expand and couple to an inner wall of the LA to anchor the device 100 within the LA. The rim may be made of the same or similar material as the web members 134 and, as such, may be self-expanding. However, the rim 136 may define a larger outer diameter such that the web members 134 are drawn outwardly in a bell or flare shape within the left atrium creating a diameter larger than the defect and causing the proximal portion to be anchored within the left atrium.

With continued reference to FIGS. 1A-1C, the central portion 120 may extend between the proximal 130 and distal 110 portions. The central portion 120 may have a generally tubular shape extending between the proximal portion 130 and the distal portion 110. The central portion 120 may be configured to direct blood flow from the right upper PV toward the LA. That is, the central portion 120 may be configured to bridge a gap and provide a conduit between the right upper PV and the LA to direct blood flow across or through the RA. The central portion 120 may thus be configured to rigidly maintain its shape and to prevent leakage into the RA. The central portion 120 may have a length L2 of between approximately 1 mm and approximately 30 mm, or between approximately 5 mm and approximately 20 mm, or between approximately 10 and approximately 15 mm. Where the central portion 120 couples to the proximal portion 130, the central portion may have diameter D2. Where the central portion 120 couples to the distal portion 110, the central portion may have diameter D4. In some embodiments, diameters D2 and D4 may be the same.

The central portion 120 may be configured to maintain a rigid tubular shape despite forces on the central portion from blood flowing therethrough or from blood flow within the RA, for example. In some embodiments, the central portion 120 may have a plurality of elongate rods 126, such as metal rods. The rods 126 may be arranged in a parallel formation along the length of the central portion 120, between the proximal 130 and distal 110 portions. The rods 126 may be rigid and may be configured to maintain their shape to span a gap between the right upper PV and the LA. In some embodiments, the rods 126 may be constructed of Nitinol. In other embodiments, the rods may be constructed of other suitable materials. Additionally, the central portion 120, or a portion thereof, may have a coating or covering arranged over or across the rods 126 so as to prevent leakage between the rods. However, in other embodiments, the rods 126 may be arranged over or across the coating material. In some embodiments, the coating may be or include polytetrafluoroethylene and/or another suitable medical grade material.

The central portion 120, or a portion thereof, may be configured to expand. For example, at its connection to the proximal portion 130, the central portion 120 may be configured to expand to diameter D2', as shown in FIG. 1C. At its connection to the distal portion 110, the central portion 120 may be configured to expand to diameter D4'. As the central portion 120 expands, the rods 126 may generally move apart from one another. Likewise, as the central portion 120 is compressed or collapsed, the rods 126 may move closer to one another. The polytetrafluoroethylene or another coating may be configured to be taught or smooth over the bars 126 when the central portion 120 is fully expanded. When contracted, the coating may form a wave-like or bunched up fabric shape between the compressed rods.

In some embodiments, the central portion 120 may have one or more stiffeners 121 configured to maintain a tubular shape in the central portion. For example, the central portion 120 may have a single centrally-arranged stiffener 121, as shown in FIGS. 1A-1C. However, in other embodiments, the central portion 121 may have more or fewer stiffeners 121. Each stiffener 121 may be or include a rigid circular wire or bar. The stiffener 121 may be arranged circumferentially around or within the central portion 120, and may couple to the plurality of parallel rods 126. In this way, the stiffener 121 may help hold the rods 126 in a rigidly tubular shape. In one or more embodiments, the stiffener may have an oval or eyelit shape in its collapsed position and a relatively round shape in its expanded condition.

The central portion 120 may have an aperture 128 extending through a wall of the central portion. The aperture 128 may be arranged between two rods 126, for example, and may remain uncoated by the coating material. The aperture 128 may be configured to provide for side branch stenting in case of the need for extra support or for bifurcating drainage. For example, where the defect results in there being two PV elements that drain into the RA and need to be addressed, the aperture 128 may allow for directing draining from both PV elements through the device 100. The aperture may have a width or diameter of between approximately 1 mm and approximately 10 mm. In some embodiments, the aperture 128 may have a width or diameter of approximately 5 mm. A sidewall or edge of the aperture 128, or a portion of the central portion 120 wall surrounding the aperture, may be radio-opaque. The edge or area immediately surrounding the aperture 128 may be radio-opaque.

The aperture 128 may allow a secondary line to be coupled to the device 100 so as to accommodate a blood flow from another branch of a branched PV, for example. It is to be appreciated that the aperture 128 may be arranged near an end of the central portion 120, such as adjacent the proximal portion 130 or adjacent the distal portion 110. In this way, the aperture 128 may be arranged on the central portion 120 such that, when not in use, the aperture may be arranged within the right upper PV or within the LA so as to prevent blood from leaking through the aperture and into the RA.

With continued reference to FIGS. 1A-1C, the distal portion 110 may be arranged and configured such that, as a medical professional inserts the device 100 into the right PV, the distal portion may be furthest from the medical professional. The distal portion 110 may have a generally tubular shape extending between the central portion 120 and the second end 122. The distal portion 110 may be configured to be arranged within the right upper PV so as to direct blood flow from the right upper PV toward the LA. The distal portion 110 may have a length L1 of between approximately 5 mm and approximately 40 mm, or between approximately 10 mm and approximately 30 mm, or between approximately 15 mm and approximately 20 mm. Where the distal portion 110 couples to the central portion 120, the distal portion may have diameter D4. At the second end 122 of the device 100, the distal portion 110 may define an opening 119 having a diameter D1. In some embodiments, each diameter D4, D1 may be between approximately 0.5 cm and approximately 4 cm. In some embodiments, diameters D4 and D1 may be the same.

The distal portion 110 may be constructed of one or more flexible materials. Additionally, distal portion 110 may be configured to expand and/or contract. For example, the distal portion 110, or a portion thereof, may be constructed of an expandable mesh material comprising a plurality of interlocking web members 125 or wires arranged in a grid formation. The web members 125 may be metal bars or wires, such as Nitinol members, in some embodiments. In other embodiments, the web members 125 may be constructed of other suitable materials. The web members 125 may be similar to web members 134 discussed above with respect to the proximal portion 130. In some embodiments, the distal portion 110 may have a coating, such as a polytetrafluoroethylene coating, over at least a portion of the length thereof so as to prevent leakage between the web members 125. In some embodiments, a portion of the distal portion 110 nearest the central portion 120 may be coated. For example, approximately ⅕, ¼, or ⅓ the length of the distal portion 110 nearest the central portion 120 may be coated. In some embodiments, approximately half the length of the distal portion 110 may be coated. In still other embodiments, more than half or all of the distal portion 110 may be coated. In some embodiments, a covering on the distal portion 110 may be an extension or continuation of a covering of the central portion 120, and may be arranged at a proximal end of the distal portion.

The mesh material, or other expandable material(s), may allow the distal portion 110, or a portion thereof, to expand and contract radially. For example, the interlocking web members 125 may be configured to expand apart, thus increasing gaps or openings between the bars and causing the distal portion to expand radially. FIGS. 1B and 1C show the distal portion 110 in an expanded configuration with expanded diameters D4' and D1'. The expanded diameter D1' of the opening 119 may be between approximately 5 mm and approximately 30 cm, or between approximately 10 cm and approximately 15 cm. The expanded diameter D4' may occur at or near a connection between the distal portion 110 and the central portion 120.

In some embodiments, the distal portion 110 may be configured to expand automatically. For example, distal portion 110 may have a tendency to expand when not being actively compressed. In some embodiments, when compressed, distal portion 110, or portions thereof, may have a wave-shaped or zig-zagged perimeter wall. The wave-shape may be a function of compression of the interlocking web members 125. In some embodiments, the distal portion 110 may be configured to expand when positioned in the right PV to occlude the sinus venosus atrial septal defect.

The distal portion 110 may be configured to be arranged within right upper PV, or within a portion thereof, so as to direct a blood flow path from the right upper PV, across the RA and into the LA. In some embodiments, the distal portion 110 may be configured to engage with, or anchor to, an inner wall or edge of the right upper PV so as to maintain a desired position of the device 100. In this way, the mesh material may be configured to attach or anchor into an inner wall of the right upper PV.

With continued reference to FIGS. 1A-1C, in some embodiments, the device 100 may be configured to couple to, or engage with, a balloon catheter or other insertion device. For example, in some embodiments, the device 100 may have one or more keyholes 116 for receiving one or more keys arranged on a balloon catheter. In particular, the distal portion 110 may have one, two, three, four, or more keyholes 116 arranged thereon. Each keyhole 116 may be arranged on a receiving plate 114. Each plate 116 may be an elongated metal plate configured to position, and provide structure to, one or more keyholes 116. The receiving plates 114 may each have any suitable shape. In at least one embodiment, the distal portion 110 may have three receiving plates 114, each receiving plate having a keyhole 116. Each keyhole may extend through the receiving plate 114 and through the mesh or other wall material of the distal portion 110. Each keyhole 116 may be shaped and configured to receive a corresponding key of a balloon catheter or other insertion device for inserting the device 100. As shown in FIG. 1B, in at least one embodiment, each keyhole 116 may have a circular first portion 117a and a rectangular second portion 117b extending laterally from the first portion. The circular first portion 117a may be configured for receiving a corresponding key inserted therein, and the rectangular second portion 117b may be configured for locking the corresponding key therein after insertion through the first portion. The first 117a and second 117b portions may be arranged such that a corresponding key may slide from each portion to the other. However, in other embodiments, each keyhole 116 may have any other suitable shape.

Figure 2:
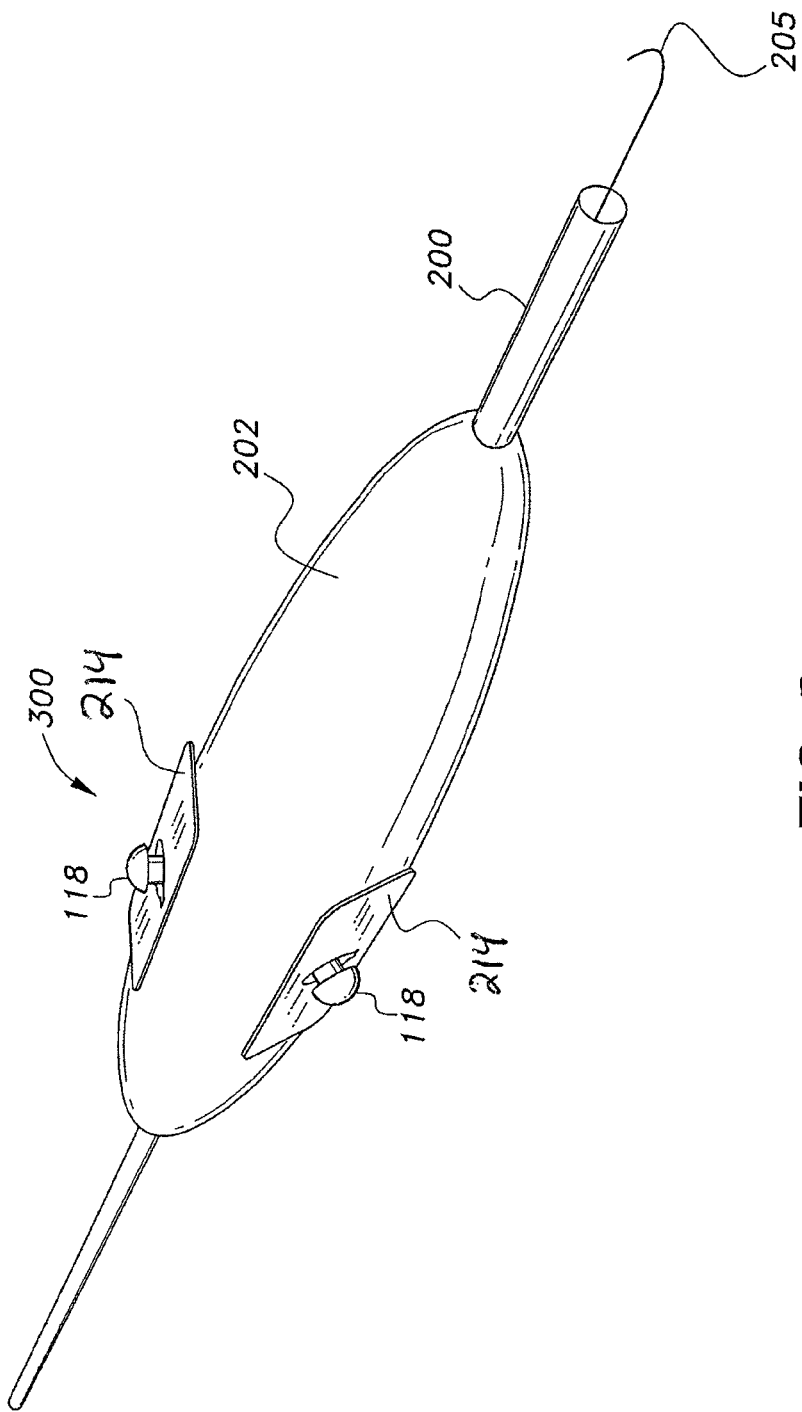
FIG. 2 illustrates a balloon catheter with a locking system for securing the atrial septal defect treatment device to the balloon of a balloon catheter, according to one or more embodiments.

Turning now to FIG. 2, a balloon catheter 200 for inserting, positioning, and/or removing the device 100 is shown, according to one or more embodiments. The balloon catheter 200 may be configured to receive a guidewire 205 extending therethrough. Additionally, the balloon catheter 200 may include a balloon portion 202 configured to inflate or expand when saline, or another suitable fluid or gas, is passed therethrough. The balloon portion 202 may generally be sized and shaped so as to be arranged within the device 100.

In some embodiments, the balloon catheter 200 may include a locking system 300 for securing the above-described device 100 to the catheter 200. The locking system 300 may include one or more keys 118 extending from the balloon 202 or from another portion of the balloon catheter 200. Each key 118 may be sized and configured to extend through a corresponding keyhole 116 arranged on the device 100. In some embodiments, each key 118 may be arranged on a locking plate 214. Each locking plate 214 may provide support for one or more keys 118 and may be configured to align with a corresponding receiving plate 114 of the device. Each locking plate 214 may have any suitable size and shape. In some embodiments, the locking system 300 may include one, two, three, four, or more keys 118, each arranged on a corresponding locking plate 214.

Each key 118 may be sized and configured to extend through a corresponding keyhole 116 of the device 100. In some embodiments, each key 118 may have a mushroom shape with a stem portion extending from the locking plate 114 and a head portion arranged at an opposing end of the stem portion. The stem portion of each mushroom-shaped key 118 may be sized and configured to fit or be arranged within the rectangular or second portion 117b of a corresponding keyhole 116. The head portion of each mushroom-shaped key 118 may be sized and configured to extend through the circular or first portion 117a of the keyhole 116, but may be sized larger than the rectangular or second portion 117b of the corresponding keyhole 116. That is, the head portion of the key 118 may be configured so as to be unable to pass through the second portion 117b. In this way, the keys 118 and corresponding keyholes 116 may be configured to lock the device 100 onto the balloon catheter 200. When the keys 118 are arranged through corresponding keyholes 116 of the device 100, a twisting of the balloon catheter 200 with respect to the device 100 may cause the stem portions of the keys to engage the second portions 117b of the keyholes, thus locking the device to the catheter. Similarly, a twisting in an opposing direction may cause the stem portions of the keys 118 to disengage from the second portions 117b of the keyholes 116, thus unlocking the device 100 from the catheter 200. In some embodiments, the keys 118 may be retractable.

Figure 3:
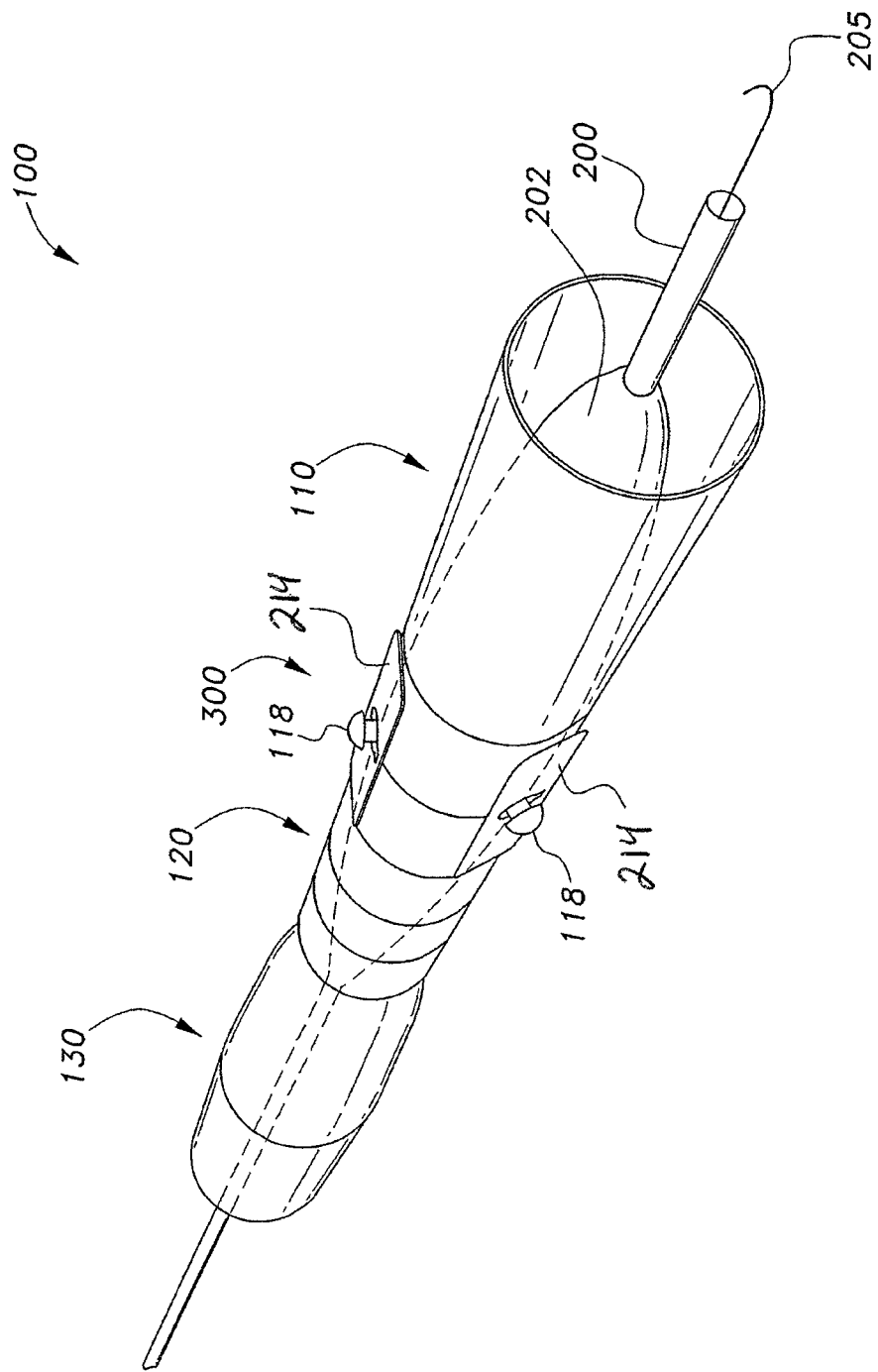
FIG. 3 illustrates the atrial septal defect device of FIG. 1A positioned on a balloon catheter positioned on a guide wire, according to one or more embodiments.

FIG. 3 illustrates the device 100 arranged over the balloon catheter 200, according to one or more embodiments. As shown, the keys 118 may extend through the keyholes 116 and beyond a diameter of the device 100. It is to be appreciated that, when the device 100 is locked to the balloon catheter 200 via the locking system 300, and the balloon portion 202 is collapsed or not inflated, the device may be prevented from expanding. That is, while coupled to the collapsed balloon catheter 200 via the locking system 300, the device 100 may be generally collapsed or may be prevented from fully expanding. Moreover, in other embodiments, other locking devices may be used to secure the device 100 to the balloon catheter 200 and/or to a different insertion tool.

In use, a device 100 of the present disclosure may be positioned to direct blood flow from a right upper PV to the LA to treat a sinus venosus atrial septal defect. A balloon catheter 200 and locking system 300 of the present disclosure may be used to percutaneously insert and position the device 100. In general, the septal defect may be accessed through the inferior vena cava (IVC), and the device 100 may be directed through the LA, and across the RA to reach the right upper PV.

It is to be appreciated that methods of the present disclosure may provide a particularized way of treating a sinus venosus atrial septal defect. That is, where many conventional methods contemplate approaching the defect from the right atrium, methods of the present disclosure may include approaching the defect from the left atrium. According to methods of the present disclosure, although a portion of the upper PV may be missing, a healthcare professional may approach the defect as if intending to place a stent in an intact PV. In this way, methods of the present disclosure may include approaching the defective upper PV from the left atrium, at an outlet where the vein drains into the atrium. Methods of the present disclosure may generally include inserting a treatment device of the present disclosure into the upper PV through its outlet in the left atrium, and positioning the treatment device to bridge gaps or openings in the PV, thus providing an artificial wall for the PV where needed. In this way, methods of the present disclosure may be fundamentally different than conventional methods of treating a sinus venosus atrial septal defect.

Figure 4:
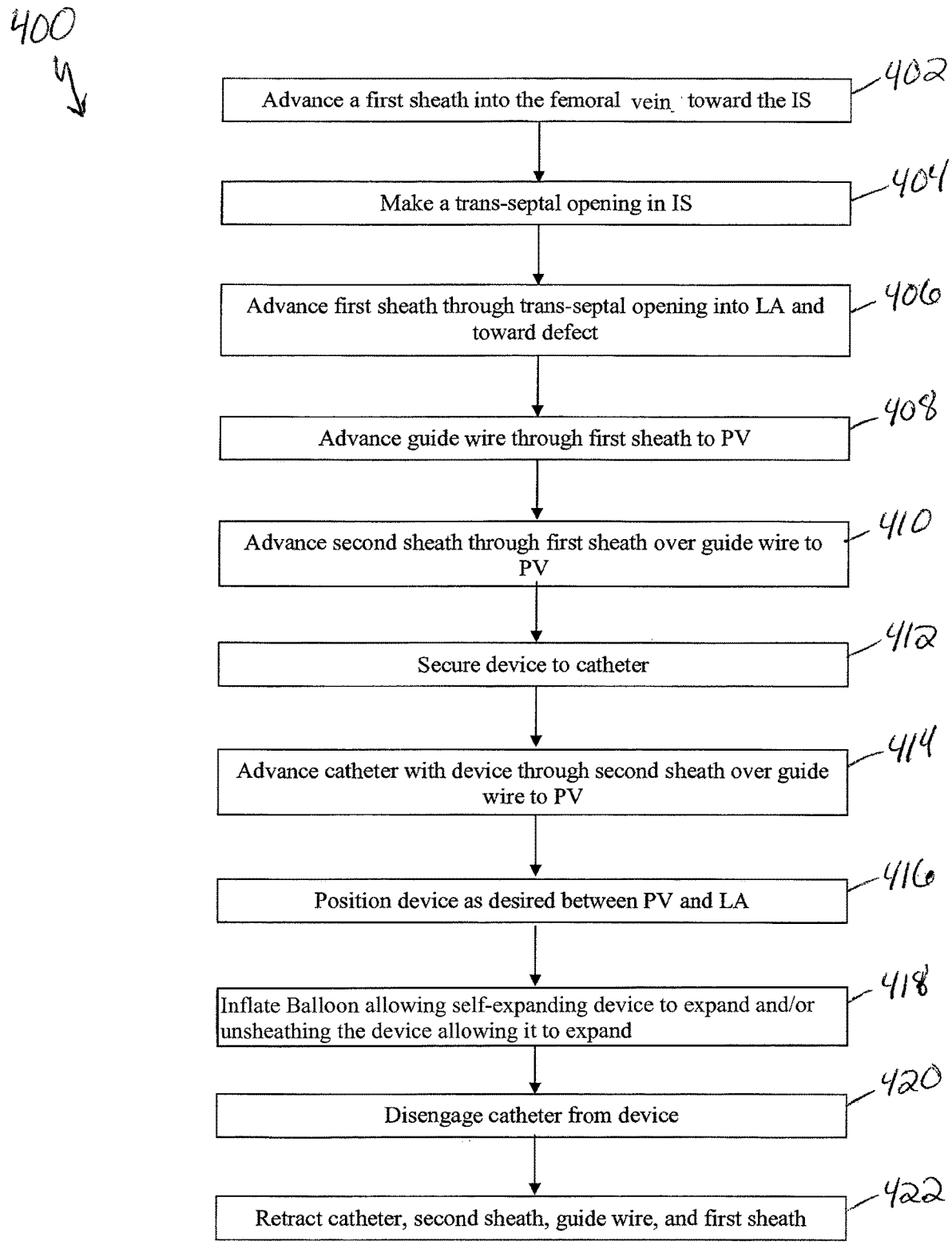
FIG. 4 is a flow diagram of a method of treating a sinus venosus atrial septal defect, according to one or more embodiments of the present disclosure.
Figure 5:
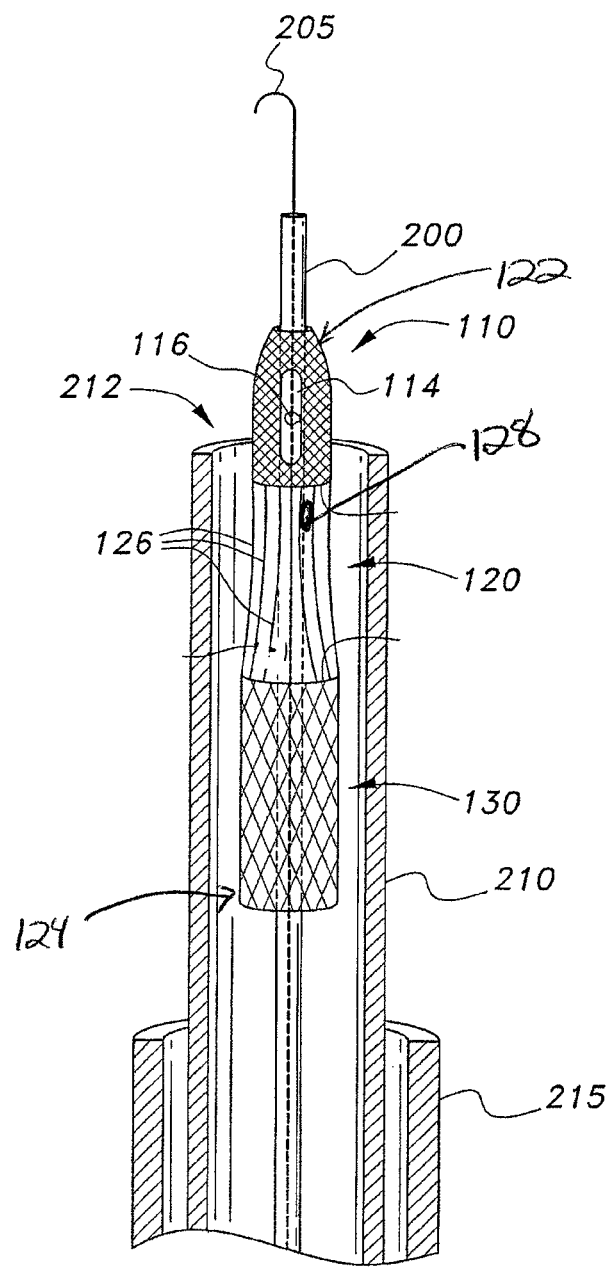
FIG. 5 illustrates an internal view of an atrial septal defect treatment device of the present disclosure secured to a balloon catheter, and arranged on a guidewire within a first sheath and a second sheath, according to one or more embodiments.
Figure 6:
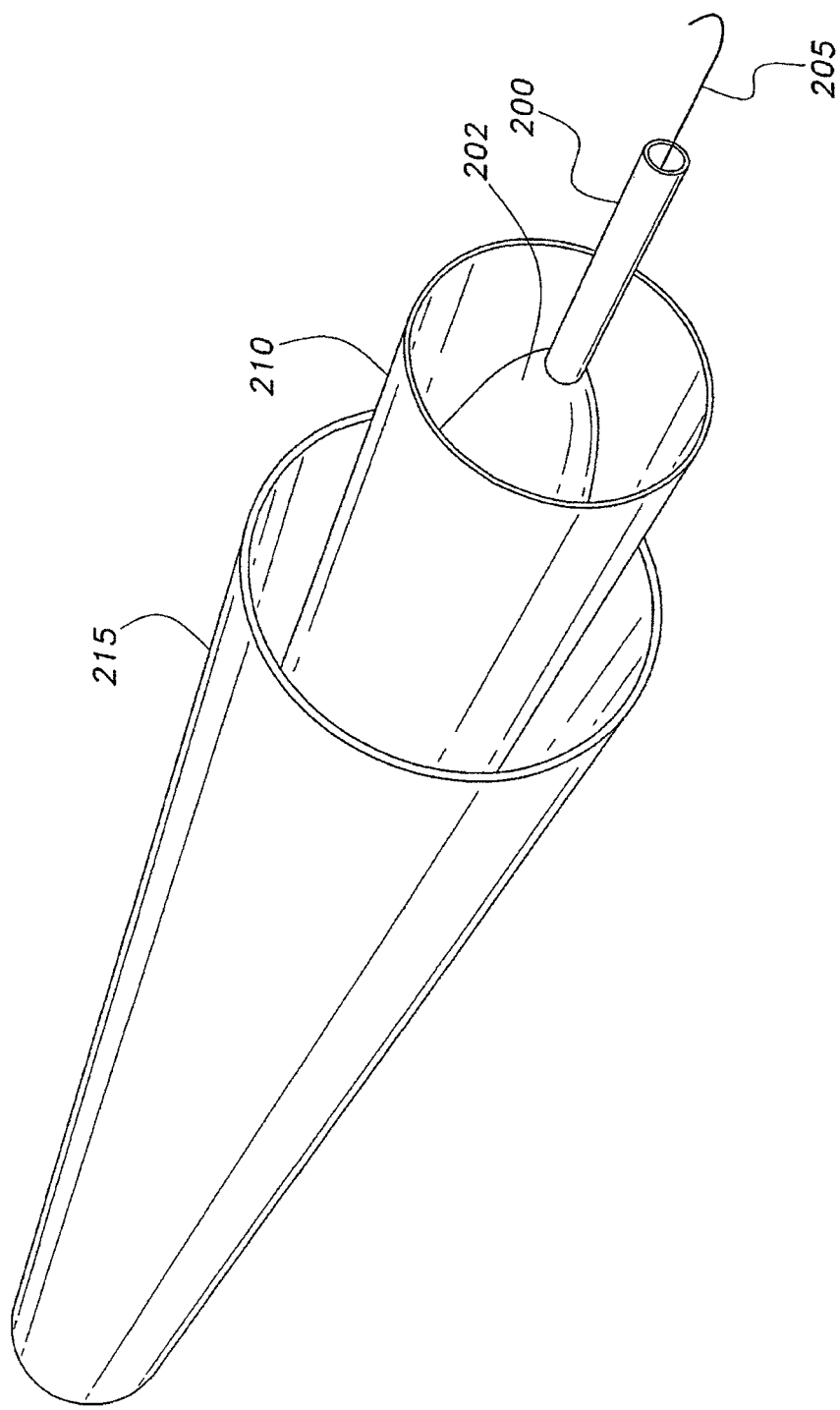
FIG. 6 illustrates a perspective view of a balloon catheter of the present disclosure arranged on a guidewire within a first sheath and second sheath, according to one or more embodiments.

Turning now to FIG. 4, a method 400 of positioning a septal defect device 100 of the present disclosure is shown, according to one or more embodiments. The method 400 may include a trans-femoral vein approach. For example, to prepare for positioning the septal defect device, the method 400 may include advancing a first sheath into the femoral vein toward the interatrial septum (IS) 402; making a trans-septal opening in the IS 404; advancing the first sheath through the trans-septal opening into the LA and toward the septal defect 406; advancing a guide wire through the first sheath to the PV 408; and advancing a second sheath through the first sheath over the guide wire to the PV 410. To insert and position the septal defect device, the method 400 may further include securing the septal defect device to the a balloon catheter 412; advancing the catheter with the device through the second sheath over the guide wire to the PV 414; positioning the device as desired between the PV and LA 416; inflating the balloon catheter to expand the device 418; and disengaging the catheter from the device 420. The method 400 may additionally include retracting the catheter, second sheath, guide wire, and first sheath 422. In other embodiments, the method 400 may include additional or alternative steps.

Additionally, the method 400, or portions thereof, may be performed with the use of imaging. For example, a trans-esophageal echocardiogram may be used to help visualize the procedure or portions thereof. Moreover, the method 400 may be performed while the patient is under general anesthesia in some embodiments.

With continued reference to FIG. 4, as indicated above, the method 400 may include advancing a first sheath into the femoral vein toward the IS (402). The first sheath 215, which may be an outer sheath, may be seen in FIGS. 5-8B. In this manner, the PV may be targeted via the IVC, as illustrated by arrow A in FIG. 7. The sheath 215 may be configured for supporting and providing access into the PV from the LA, via the IS. The first sheath 215 may be a relatively large caliber deflectable and/or steerable sheath in some embodiments. The first sheath 215 may have a size of between 9 Fr and 12 Fr in some embodiments. In some embodiments, the first sheath 215 may be a steerable sheath such as the Agilis™ NXT Steerable Introducer from St. Jude, the Flex-Cath Advance Steerable Sheath from Medtronic, or the Vado® Steerable Sheath from Abbott. The first sheath 215 may be advanced through the femoral vein, through the IVC. The first sheath 215 may further be advanced through the RA and toward the IS.

Figure 7:
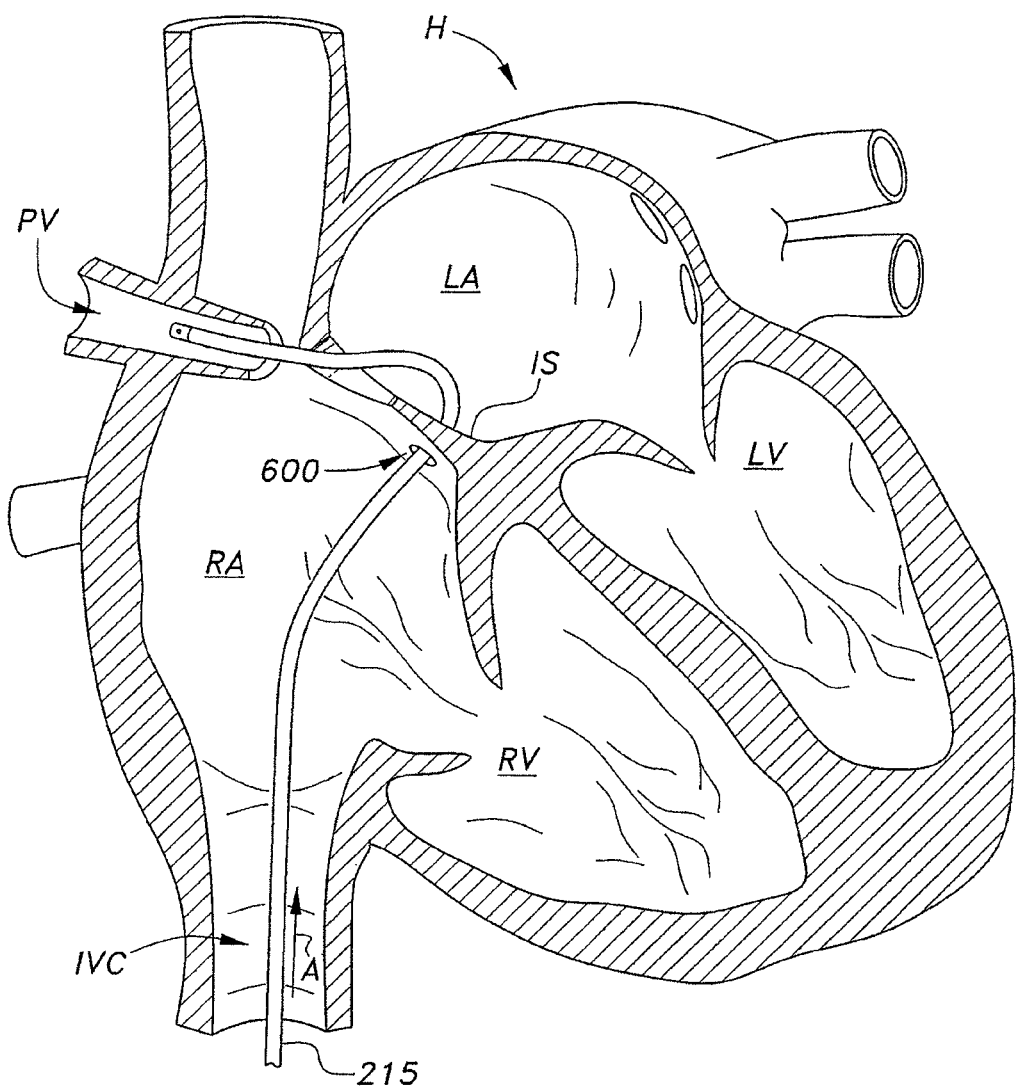
FIG. 7 illustrates an internal view of a human heart having a sinus venosus atrial septal defect and with a first sheath arranged therein, according to one or more embodiments.
Figure 8A:
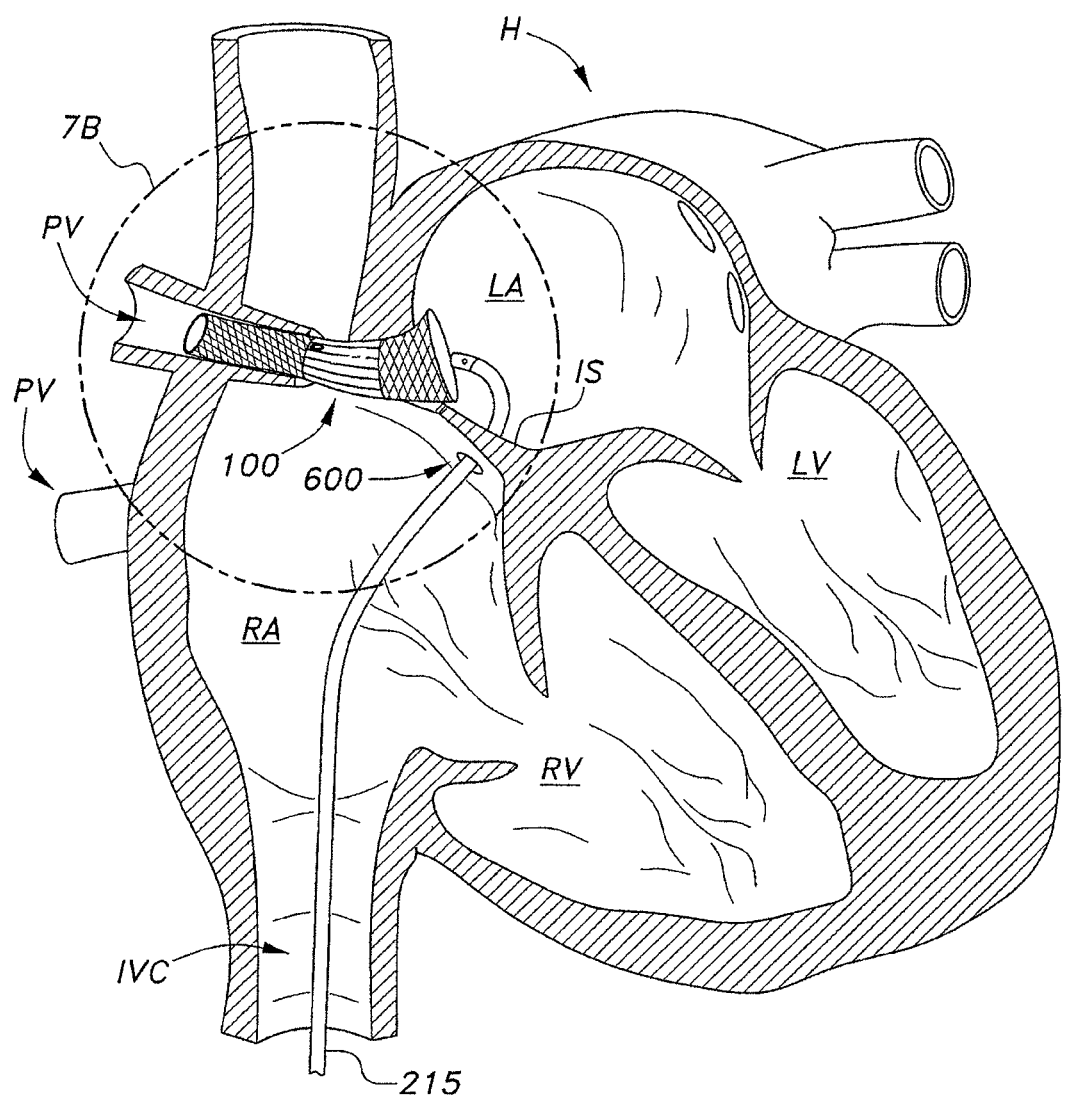
FIG. 8A illustrates another internal view of a human heart having a sinus venosus atrial septal defect and with a treatment device of the present disclosure arranged therein, according to one or more embodiments.
Figure 8B:
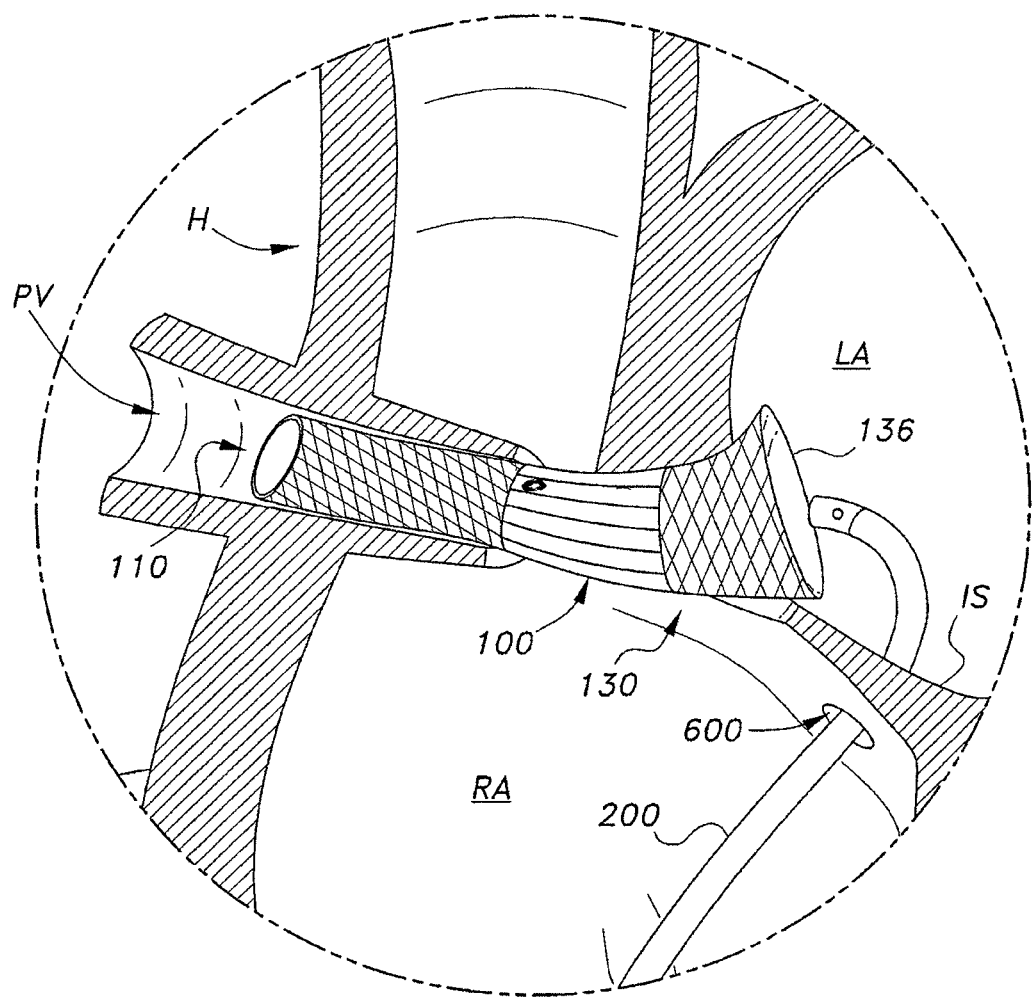
FIG. 8B is a close-up view of the treatment device arranged in the sinus venosus atrial septal defect of FIG. 7A, according to one or more embodiments.

To pass the first sheath 215 into the LA, a trans-septal opening may be cut in the IS (504). The opening 600 in the IS, according to one or more embodiments, may be seen in FIGS. 7-8B. The opening may be made by advancing a trans-septal needle through the first sheath 215 toward the IS and extending the needle from the first sheath to puncture the IS. The opening 600 may be sized to receive the first sheath 215. Additionally, the opening 600 may be positioned in the IS at a point below the septal defect so as to allow for the first sheath 215 to reach the defect once through the opening 600. The trans-septal opening 600 may allow for vascular access, as well as access into the target PV. Where a trans-septal needle or other device was advanced through the first sheath 215 to make the opening 600, the needle may be withdrawn from the sheath. With the opening 600 made, the first sheath 215 may be advanced through the trans-septal opening and into the LA toward the septal defect (406). As shown in FIG. 7. The first sheath 215 may be extended into the target PV.

The method 400 may further include advancing a guide wire through the first sheath 215 to the PV (408). The guide wire 205 may be seen in FIGS. 5 and 6. The guide wire 205 may be configured to provide an axis along which additional components may be advanced through the first sheath 215. The guide wire 205 may be an elongated stiff "J" tip guide wire in some embodiments. The guide wire 205 may be advanced into the target PV. With the guide wire 205 in place, a second sheath may be advanced through the first sheath 215 and over the guide wire (410). The second sheath 210, which may be an inner sheath, may be seen in FIGS. 5 and 6. The second sheath 210 may have a diameter smaller than that of the first sheath 215, such that it may be passed through the first sheath. Additionally, the second sheath 210 may be sized to receive the catheter and septal defect device. In some embodiments, the second sheath 210 may have a radio-opaque marker arranged at, for example, a tip or end 212 of the second sheath. The radio-opaque marker may help a medical professional identify a location of the second sheath 210. The second sheath 210 may be advanced into the target PV.

To position the septal defect device 100, the device 100 may be secured to a balloon catheter 200 (412). As described above and shown in FIG. 3, a locking system 300 may be used to secure the device 100 to a balloon catheter 200. The catheter 200 may be passed through the device 100 such that the device is arranged over the balloon portion 202. The catheter 200 and/or device 100 may be rotated as needed to align the keys 118 with the keyholes 116. The keys 118 may be extended through the keyholes 116, and the catheter 200 may be rotated with respect to the device 100 to lock the keys in the keyholes (or the device may be rotated with respect to the catheter. However, as indicated above, in other embodiments, other locking systems may be used to secure the device 100 to the balloon catheter 200.

While the device 100 is secured or locked to the balloon catheter 200, the balloon portion 202 may operate to collapse the sidewall of the device, or to prevent the device from expanding. As described above, the device 100 may be configured to expand automatically when not restricted or compressed. Thus, by attaching the device 100 to the balloon catheter 200, the drained balloon portion 202 may pull the sidewall of the device inward toward a central axis of the device. This may keep the device 100 from expanding while it is inserted and positioned as desired between the upper PV and LA. As described below, once the device 100 is positioned as desired, the inner sheath may be pulled proximally to unsheathe the device causing it to self-expand. The balloon catheter 200 may be inflated to allow the device to expand. In other embodiments, however, other mechanisms for restricting or collapsing the device 100 may be used during insertion and positioning of the device.

With the device 100 secured to the catheter 200, the catheter and device may be advanced along the guide wire 205 and through the second sheath 210 (414). The catheter 200 may be advanced into the target PV. Additionally, the catheter 200 may be advanced so as to extend the distal portion 110 of the device 100 outside of the second sheath 210 and first sheath 215, as shown for example in FIG. 5. The method 400 may further include positioning the device 100 as desired between the PV and LA (416). The catheter 200 may be used to position the device 100 between the target PV and LA so as to bridge a gap between the PV and LA. The device 100 may be positioned such that the distal portion 110 is arranged within the target PV, and such that the proximal portion 130 is arranged within the LA. Additionally, the device 100 may be positioned such that the central portion 120 passes through the RA so as to prevent leakage of blood flow from the PV into the RA. Imaging may be used to ensure proper placement of the device. Once in a desired position, balloon portion 202 of the catheter 200 may be inflated in order to expand the device 100 (418). For example, saline or another suitable liquid may be used to inflate the catheter. Expansion of the balloon 202 may cause at least the distal portion 110 of the device 100 to expand. As the balloon 202 and device 100 expand, the distal portion 110 may expand within the target PV to reach an inner wall of the PV and anchor thereto.

The catheter 200 may be disengaged from the device 100 (420) by twisting or rotating the catheter with respect to the device, causing the keys 118 to disengage from the rectangular portions of the keyholes 116. Where other locking mechanisms are used, other disengaging operations may be performed. With the catheter 200 disengaged from the device 100, each of the catheter, second sheath 210, guide wire 205, and first sheath 215 may be withdrawn from the heart, through the IVC, and through the femoral artery (422). As the catheter 200 and sheaths 215, 210 are withdrawn, the proximal portion 130 may be free to expand into the LA to reach and anchor to a wall of the LA. It is to be appreciated that the trans-septal opening 600 may close or heal on its own over time. However, in some embodiments, the method 400 may include closing or sealing the opening 600.

In some embodiments, the method may further include extending a bridge between the aperture 128 and a branched portion of the target PV. As described above, the aperture 128 may allow the ability to accommodate a branched PV. Blood flow from one or more branches of the branched PV may be directed to the aperture 128. In one or more embodiments, the side hole may be radio-opaque and by placing the hole facing the pulmonary vein, blood may flow into the device lumen. In one or more embodiments, a small covered stent may be provided to extend between the branched portion of the pulmonary vein and the hold in the device. As additionally described above, the aperture 128 may be arranged near or within radio-opaque material such that imaging may be used to help locate the aperture. However, where the target PV is not branched, or where the aperture 128 will otherwise not be used to bridge a branched PV, imaging may be used to position the device 100 such that the aperture 128 does not leak into the RA. In particular, at step 416, the device 100 may be arranged with the central portion 120 partially within the PV such that the aperture 128 is positioned within the target PV or against or within a wall of the PV, so as to mitigate leakage through the aperture into the RA. In other embodiments, such as where the aperture 128 is arranged nearer the proximal portion 130 than the distal portion 110, the device 100 may be arranged with the central portion 120 partially in the LA such that the aperture 128 is positioned in the LA or within or against a wall of the LA to prevent leakage through the aperture.

It is to be appreciated that an advantage of the devices and methods of the present disclosure is that the procedure may be generally reversible. That is, if the treatment is ineffective or if there is an adverse effect or any other reason to reverse the treatment, the device 100 may be removed percutaneously. Removal of the device may include extending, via a sheath and guide wire, a balloon catheter 200 through the femoral vein, IVC, RA, through a trans-septal opening, and into the device 100 from the proximal portion 130. The balloon portion 202 of the catheter may be expanded such that the keys 118 of the locking system 300 may engage the keyholes 116 of the device 100. The catheter 200 may be rotated to lock the keys 118 in place, as described above. Additionally, removal may include draining or partially draining the balloon portion 202 so as to contract the device 100 or a portion thereof. With the device 100 contracted, it may be pulled to remove the distal end from the pulmonary vein and the distal end may remain in the right atrium. At that point, the device may be reverse captured by removing the balloon and catheter and accessing the right atrium and capturing the device via its distal end. In this manner, a catheter may be advanced over the device via the collapsed distal end so as to start at the smaller end and advance fully over the device including the proximal end and the augmenter rim. In other embodiments, other retrieval methods may be used to remove the device 100. For example, the device 100 may be removed through the upper right PV, rather than through the LA.

Devices and methods of the present disclosure provide an improved treatment for an atrial septal defect. The devices and methods provide an improvement over conventional methods of treating such septal defects because the devices and methods described herein allow for a percutaneous solution, which may be far less invasive than conventional treatment methods. As such, treatment devices and methods of the present disclosure may provide for relatively faster recovery times and fewer complications, as compared with conventional treatments. Additionally, atrial septal defect treatment devise and methods described herein may be reversible. Whereas other methods for treating such defects may be difficult or impossible to fully reverse once implemented, a device of the present disclosure may simply be removed if necessary. Moreover, it is to be appreciated that devices of the present disclosure are configured for relatively simple implantation and removal using a balloon catheter to control expansion and collapse of the device. It is further to be appreciated that, once in place between a target PV and a LA, a device of the present disclosure may be configured to hold its shape so as to provide a conduit between the PV and LA. In particular, a central portion 120 of a device 100 of the present disclosure may be configured to maintain its tubular shape while positioned within the RA, between the PV and LA.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

Additionally, as used herein, the phrase "at least one of [X] and [Y]," where X and Y are different components that may be included in an embodiment of the present disclosure, means that the embodiment could include component X without component Y, the embodiment could include the component Y without component X, or the embodiment could include both components X and Y. Similarly, when used with respect to three or more components, such as "at least one of [X], [Y], and [Z]," the phrase means that the embodiment could include any one of the three or more components, any combination or sub-combination of any of the components, or all of the components.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A method of treating a sinus venosus atrial septal defect in a patient, the method comprising:
    advancing a sheath through a femoral vein and inferior vena cava of the patient, toward an interatrial septum of the patient;
    from a right atrium of the patient, making a trans-septal opening in the interatrial septum; and
    from a left atrium of the patient, positioning a hollow lumen between the left atrium and a pulmonary vein of the patient to bridge the sinus venosus atrial septal defect.

2. The method of claim 1, wherein positioning a hollow lumen between the left atrium and a pulmonary vein of the patient comprises arranging a distal portion of the lumen in the pulmonary vein and arranging a proximal portion of the lumen in the left atrium, wherein a central portion of the lumen is arranged within the right atrium to provide a conduit for blood flow between the pulmonary vein and the left atrium.

3. The method of claim 1, further comprising using imaging to visualize the hollow lumen within the patient.

4. The method of claim 1, wherein the lumen comprises a sidewall aperture and wherein the pulmonary vein is branched, the method further comprising extending a bridge between a branch of the pulmonary vein and the aperture so as to provide a conduit for blood flow from the branch of the pulmonary vein to the treatment device.

5. The method of claim 1, wherein the patient is under general anesthesia.

6. The method of claim 1, further comprising sealing the trans-septal opening.

7. The method of claim 1, wherein the hollow lumen is removable, and the method further comprises accessing the hollow lumen through the left or right atrium to remove the hollow lumen by capturing the hollow lumen through a locking mechanism.

8. The method of claim 1, further comprising positioning the lumen over a balloon catheter and inflating the balloon catheter to expand a diameter of the lumen.

9. The method of claim 8, further comprising locking the lumen to the balloon catheter and, after the lumen is positioned between the left atrium and a pulmonary vein of the patient and inflated, disengaging the lumen from the balloon catheter.

* * * * *